United States Patent [19]

Tognella et al.

[11] Patent Number: 4,871,528
[45] Date of Patent: Oct. 3, 1989

[54] PHARMACEUTICAL COMPOSITIONS HAVING ANTINEOPLASTIC ACTIVITY

[75] Inventors: Sergio Tognella; Michele Tedeschi; Roberto Assereto; Odoardo Tofanetti; Ennio Cavalletti, all of Milan, Italy

[73] Assignee: Boehringer Biochemia Robin SpA, Milan, Italy

[21] Appl. No.: 105,169

[22] Filed: Oct. 7, 1987

Related U.S. Application Data

[63] Continuation-in-part of Ser. No. 102,746, Sep. 24, 1987, abandoned, which is a continuation of Ser. No. 857,344, Apr. 30, 1986, abandoned.

[30] Foreign Application Priority Data

Oct. 7, 1986 [IT]   Italy .............................. 21925 A/86
Sep. 1, 1987 [IT]   Italy .............................. 48339 A/87

[51] Int. Cl.$^4$ ............................................ A61K 37/00
[52] U.S. Cl. ...................................... 424/10; 514/11; 514/922
[58] Field of Search .................... 424/10; 514/922, 11

[56] References Cited

FOREIGN PATENT DOCUMENTS 0265719  5/1988  European Pat. Off. .

OTHER PUBLICATIONS

Yoda et al., "Prevention of Doxorubicin Myocardial Toxicity in Mice by Reduced Glutathione," Cancer Research 46, 2551-2556, May 1986.
Zunino et al., "Protective effect of reduced glutathione Against Cis–Dichlorodiammine Platinum (II)–induced Nephrotoxicity and Lethal Toxicity", Tumori 60:105–111, 1983.
Leszynska et al., Chem. Abst. 97(13):103887b (1982).
Danysz et al., Chem. Abst. 102 (9):72513S (1985).
Danysz et al., Chem. Abst. 100 (9):61471j (1984).
Danysz et al., Chem. Abst. 102 (25):216427V (1985).
Tofametti et al., Chem. Abst. 103 (17):134586Z (1985).

Primary Examiner—Douglas W. Robinson
Assistant Examiner—Richard Kearse
Attorney, Agent, or Firm—Nikaido Armstrong

[57] ABSTRACT

Pharmaceutical compositions containing unit or separate dosages of 2.5 to 5 grams of reduced glutathione (GSH) and known anti-tumor agents, to be used simultaneously, separately or sequentially in anti-tumor therapy.

Compounds of the invention, that can be used both in mono- or polychemotherapy, reach surprising results against tumors, thus avoiding the onset of dangerous side-effects, such as nephrotoxicity induced by cis-platinum, and increasing the long term survival rates.

18 Claims, 1 Drawing Sheet

U.S. Patent     Oct. 3, 1989     4,871,528
FIG. 1
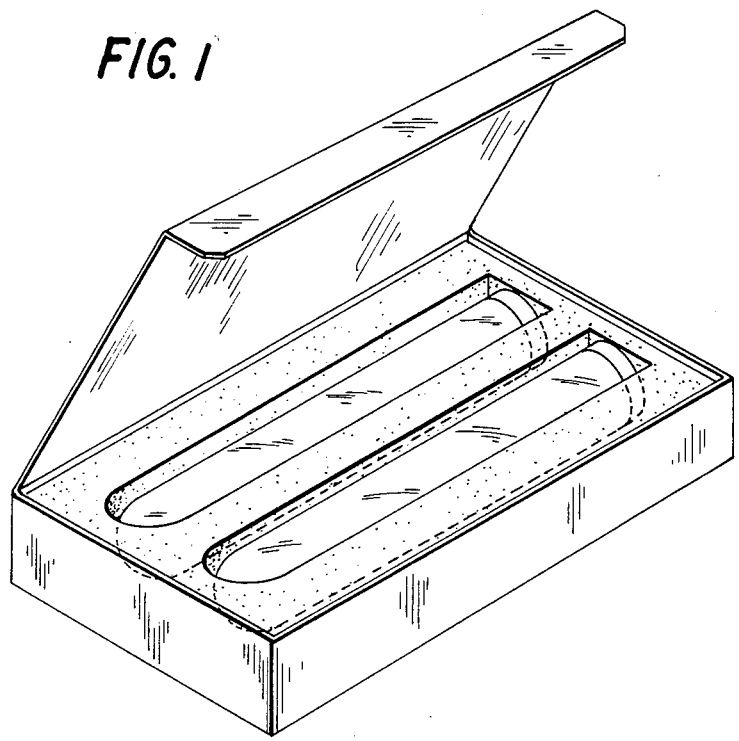
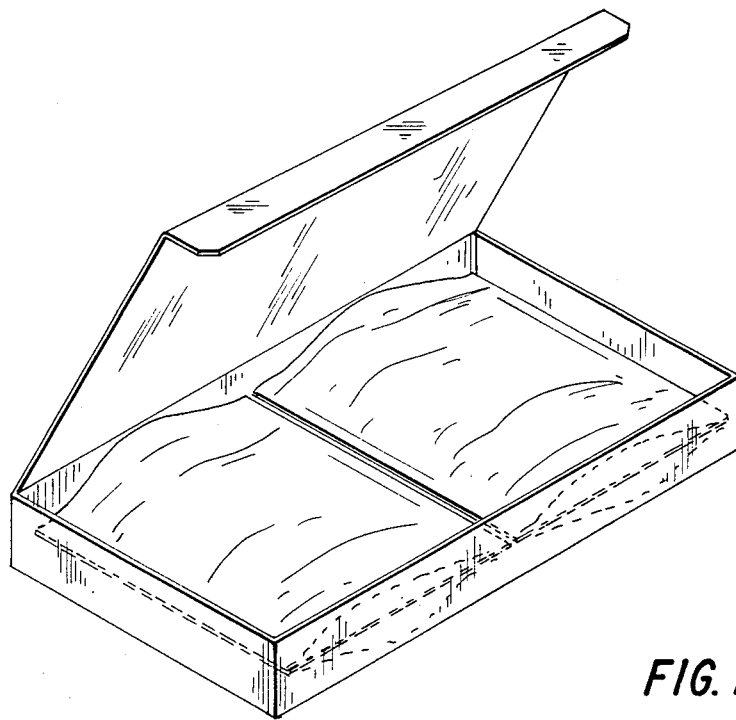
FIG. 2

PHARMACEUTICAL COMPOSITIONS HAVING ANTINEOPLASTIC ACTIVITY

This application is a continuation-in-part of earlier application Ser. No. 857,344, filed Apr. 30, 1986, now abandoned, and the 37 CFR 1.62 continuation application thereof, Ser. No. . filed Sept. 24, 1987.

FIELD OF THE SYNERGISTIC INVENTION

In one embodiment, the present invention relates to synergistic pharmaceutical compositions and methods including anti-tumor agents and reduced glutathione (GSH) as associated preparations to be used simultaneously, separately or sequentially in anti-tumor therapy.

BACKGROUND OF THE SYNERGISTIC INVENTION

Representative examples of drugs introduced in anti-tumoral chemotherapy are: cis-diamine-dichloro-platinum, also referred to as CDDP or cis-platinum, cyclophosphamide, 5-fluorouracyl, doxorubicin (adriamycin), metaxanthrone, methotrexate, etoposide, vincristine and bleomycin; each being characterized by different mechanisms of action and by different schedules of administration.

Few cancer chemotherapeutic agents are effective as single agents; most of them are often used in combination with other anti-tumoral agents so employing a variety of different mechanisms to kill malignant cells.

Polychemotherapeutic antitumoral regimens are particularly preferred for management of those tumoral forms that are refractory to a single agent (as it often happens in certain cases of solid tumors), with the aim of obtaining the highest possible index of remission of the disease and of preventing the onset of resistance to a single chemotherapeutic agent.

Each cancer chemotherapeutic agent unfortunately induces side-effects and toxicity that are often so serious to prevent the continuation of therapy, thus precluding the final success of therapeutical schemes. Combined use of anti-tumoral agents, according to the usual practice of chemotherapy, causes even more the cumulative onset of all side-effects of the single compounds.

For instance, the side-effects pattern become more serious when two or more of these compounds are used in combination or together with other anthracycline (e.g., adriamycin) or anthraquinone compounds, that have myocardiotoxicity as the most serious additional side-effect.

An attempt to improve the therapeutic possibilities in the treatment of tumors, is accomplished either by finding out new and more active agents, with a minor toxicity (see for example the new cis-platinum complexes, e.g. compounds known s NSC 311056, NSC 241240 and NSC 256927, widely experimented), or in a more immediate way by increasing the therapeutic index of compounds already available by means of treatments to be carried out simultaneously with antineoplastic agents. Up to now, the latter approach has been mainly used in order to correct and limit the side-effects inseparable from the anti-neoplastic therapy itself.

So, for example, in order to limit the dose-dependent nephrotoxic effect induced by cis-platinum in 80-90% of cases, with noticeable tubular damages shown by the increase of urinary levels of N-acetylglucosaminidase (NAG) and of alanine-aminopeptidase (AAP), the patients are subjected to a forced-hydration regimen by means of prolonged intravenous infusions with saline, glucose or mannitol solutions.

Said protective treatment, which is anyhow quite uncomfortable for the patient, is necessary, but turns out to be sometimes insufficient, especially in those cases when administration of large quantities of platinum complexes is required.

Moreover, the same protective treatment could be dangerous in case of renal insufficiency and/or in the presence of cardiovascular diseases, as a consequence of the great amounts of the fluids which are necessarily administered.

Thus, for example, prevention of toxic damages, particularly urotoxicity, induced by cytostatic oxazaphosphorinic agents is pursued by concomitant administration of mercapto-alkane-sulphonic acids as disclosed by EP No. 2495.

Otherwise, animal experiments seem to suggest that prevent and sequential administration of a natural thiol compound such as reduced glutathione ($\alpha$-glutamyl-glycinyl-cysteine) could be useful for preventing renal- and urotoxicity induced by both the anti-tumoral agents: cyclophosphamide and cis-platinum (see for example Tumori 69. 105 (1983) and cancer, Chemother., Pharmac. 14, 188, 1985). Unfortunately, the extremely high dosages of GSH (from 200 mg/kg up to 4 g/kg in divided doses) used in said experimental studies for achieving some beneficial effects rules out any real utility of this natural thiol in the clinical practice.

Useful doses in men would require the administration of 15-280 g administration of 15-280 g of GSH, adding serious practical problems to those already perceived during hydration regimen.

Current knowledges (ride infra), looking at the lowering of intracellular GSH level as a therapeutical aim to be pursued in order to favour antineoplastic therapy, furtherly discourages this approach.

On the contrary, reduced GSH has been recently proposed as effective and clinically useful protecting agent in men towards side-effects (particularly tubular damages) of platinum complexes and particularly "cis-platinum", (Italian patent application No. 20591 A/85 of 6th May, 1985) when administered in a dose range from 2.5 to 5 g as total dose for each side-effects preventive treatment by infusional route.

Said treatment, not changing the hydration regimen, is claimed to limit tubular damages, as shown by NAG and AAP enzymes determination in urine, without significant detrimental effects on anti-tumor activity.

All these known treatments do not allow however the increase of administration dosages of anti-tumoral compounds to the level that should be necessary in particular conditions of natural or induced resistance (for example in most cases of solid tumors, in particular those of the lungs and colon).

A great effort has been recently made to find substances which are able to restore the sensitivity of resistant cells to drugs such as doxorubicin, vincristine, cis-platinum, and which can possibly increase the cytotoxicity.

So, for example, calmodulin, an ubiquitous calcium-binding protein, responsible for many of the intracellular actions of calcium, was recently proposed as a potential target for cancer chemotherapeutic agents, (W. H. Hait J. of Clin. Oncol. 4, 994 (1986). Some calmodulin antagonists are themselves cytotoxic substances and various trials are running to prove if their inclusion in traditional cytotoxic chemotherapeutic regimens may extend the efficacy of the currently available drugs.

Recent studies have also concentrated on the use of calcium channel blockers in combination with classical cancer chemotherapeutic agents.

On the other hand, the use of buthionine sulphoximine as a specific agent for depletion of GSH from cells has been proposed by Andrews et al. in Cancer Res. 45, 6250, 1985 to enhance the cyto-toxic activity of compounds such as L-phenylalanine mustard, chlorambucyl, CDDP, mechlorethamine, carboplatin, diclorethylendiamine-platinum (II), 1,2-diamino-cyclohexyl platinum [II]-malonate.

SUMMARY OF THE SYNERGISTIC INVENTION

Surprisingly, and in contradiction to the above mentioned teachings, we have now found that merely a treatment with GSH, which for itself does not have cytotoxic activity, in combination with various anti-tumor agents, such as platinum compounds, oxazaphosphorinic compounds, 5-fluoro-uracil, methotrexate and anthracycline compounds, in mono- or polychemotherapy, does not only protect from the onset of side-effects of said drugs, but it is also able to increase the response rate, i.e. remission, allowing an increase of recoveries (long-lasting remissions at 2 years from the end of treatment).

DETAILED DESCRIPTION OF THE SYNERGISTIC INVENTION

One object of the invention is therefore provided by pharmaceutical compositions containing reduced glutathione (GSH) and at least one of said anti-tumoral drugs in form of combined preparations for the simultaneous, separated or sequential use in anti-tumor therapy.

According to a preferred embodiment, the invention provides a package containing GSH and the anti-tumor drug in separated vials, so that they can be administered according to the most suitable administration schemes.

The platinum compound according to the invention is preferably cis-dichloro-diamine-platinum (II). Other platinum compounds which may be used include, for instance, carboplatin, dichloro-ethylenediammine-platinum (II), 1,2-diamino-cyclohexyl-platinum-[II]-malonate or sulphate, diisopropylamino-trans-dihydroxy-cis-dichloroplatinum IV.

Oxazaphosphorinic compounds include the well known cyclophosphamide and iphosphamide.

Finally, the anthracycline compound is preferably doxorubicin (adriamycin). Other anthracycline compounds usable according to the invention include epirubicin, daunorubicin, carmamycins, mitoxanthrone, and analogs thereof.

The above compounds are usually used in combination, according to suitable protocols of polychemotherapy.

Thus, it is possible to administer a combination of anti-neoplastic agents, e.g. platinum (II) - or platinum (IV) complexes together with cyclophosphamide and methotrexate.

Of course, any other possible combination of anti-neoplastic agents mentioned in this application is also possible and lies within the knowledge of a person skilled in the art.

The administration of GSH proved to be particularly advantageous in combination with the platinum complexes.

For instance, it has been noticed that the administration of cis-platinum in combination with glutathione according to the present invention leads not only to a dramatical decrease in side-effects such as nephro- and neurotoxicity which can be normally observed when cis-platinum alone is administered, but, above all, surprisingly shows that the efficacy in anti-tumor activity expressed as remission rate and disease free survival is increased. Moreover, the administration of higher amounts of cis-platinum should be especially advantageous in those cases in which a higher dosage is required to sufficiently effect the treatment of advanced tumors. It is also surprising that the pretreatment with glutathione allows, through unknown mechanisms, to use cummulative higher amounts of cis-platinum in each course, achieving thereby a higher efficacy even in advanced stages. This was not possible when cis-platinum alone was administered due to the accompanied high toxicity and severe side-effects in connection therewith.

In fact, the maximum applicable dosage is about 1000 mg/m$^2$, which means an increase of 600–400 mg/m$^2$ in comparison to the maximum dosage of 400–600 mg/m$^2$ when cis-platinum was administered without glutathione. In the latter case severe side-effects had to be taken into consideration.

In similar manner as described above the myocardial toxicity evolved by the use of doxorubicin is decreased, when administered in combination with glutathione. A comparable effect is observed (reduced myelo- and bladder-toxicity) when cyclophosphamide or methotrexate is administered.

The most surprising aspect of the present invention is provided by the synergistic effect of GSH and the above cited anti-tumoral agents in spite of that, part of the above discussed scientific literature teaches an intracellular GSH depletion to be desirable for enhancing the antitumoral activity.

Said synergism is moreover also particularly surprising in view of the fact that GSH, administered alone, is completely devoid of any antitumoral activity.

These unpredictable effects, which could be therefore referred to as "synergism", are evident when a selected dosage regimen is used, namely 2.5 to 5 g of glutathione, approximately corresponding to 1500 mg/m$^2$–3000 mg/m$^2$ of GSH (considering the mean body surface to be about 1.4 m$^2$ *for women* and about 1.7 m$^2$ for men) whereas each anti-tumor agent is administered at the doses usually known in therapy, or higher doses, as stated above, since the administration of GSH allow to considerably increase the dose of the anti-tumor drugs, without the onset of toxicity symptoms. This often causes significant improvements in the overall therapeutic results.

Higher doses of GSH proved to be uncomfortable for the administration to patients, with possible decrease of anti-tumor efficacy, whereas lower doses induced only minor improvements in the tolerability of the anti-tumor drug.

Another important advantage of the invention, obviously when platinum compounds are used, is that forced-hydration may be drastically reduced when the patient is pre-treated with GSH.

The doses of the anti-tumoral drugs according to the invention are well known in the art, see for instance Goodman & Gilman, The Pharmacological Basis of Therapeutics VII Ed. MacMillan Pub. Co., N.Y. 1985, pp. 1240–1306, the disclosure of which is hereby incorporated by reference for the disclosure of such dose therein. For instance, as far as platinum complexes dichlorodiamineplatinum, two dosage regimens are widely used:

the first consists in the administration of 90 mg/m$^2$ at the day 1 —then 3 weeks of wash-out, followed by further 4 treatments, always every 3 weeks, reaching therefore a total dose of 450 mg/m$^2$.

The other regimen consists in administering 40 mg/m$^2$ of CDDP daily for 5 days (200 mg/m$^2$ total) and said treatment should be continued for at least 5 weeks, up to a total dose of 1 g/m$^2$. However, in the therapeutical practice, the treatment is usually interrupted after 2 or 3 cycles (400 mg/m$^2$ or 600 mg/m$^2$) because of the onset of serious side-effects, which can even be fatal.

The contemporaneous administration of 1.5 g/m$^2$ to 3 g/m$^2$ of GSH produces in both cases beneficial effects, allowing the completion of the regimen, up to the maximum permissible doses.

When cyclophosphamide or iphosphamide is used, from 0.5 g to 4 g of GSH per g of cyclophosphamide are generally sufficient, in order to obtain the effects according to the invention.

In the case of anthracyclines, with particular reference to doxorubicin, the ratio GSH/doxorubicin, is ranging from 20 to 50 mg of GSH per mg of anthracycline.

Since anthracycline is usually administered at doses ranging from 30 to 60 mg/m$^2$, the GSH dosage with doxorubicin treatment is broadly from 1 to 5 g.

A particularly surprising effect obtained by the administration of GSH with anthracycline, is the protection from myocardiotoxicity, which is a typical side-effect of this kind of drugs. Moreover, in the animal studies hereinbelow reported, it was noticed that the combination of an anthracycline and GSH is active against a strain of tumoral cells resistant to the anthracycline itself; it is therefore possible that GSH is able to modify the resistance of tumoral cells resistant to selected chemiotherapeutic drugs.

The therapeutical consequences of said effect should be highly important because it is known that the phenomenon of resistance is one of the most serious problems of anti-tumoral chemiotherapy.

As far as methotrexate is concerned, it should be noted that the clinical dosage may be remarkably variable An i.v. dose of 50/250 mg./m$^2$ is usually referred to a "low" dosage, an i.v. dose of 1–2 g/m$^2$ as an "intermediate" dosage, and 10 g/m$^2$ as a "high" dosage. In said conditions, the ratios between GSH and methotrexate are correspondingly variable, for instance from 0.3 to 15 mg of GSH per mg of methotrexate, corresponding to total GSH dosages from 1 to 5 g.

The mean weight ratios for selected anti-tumor agents are hereinbelow summarized:

| Anti-tumor agent | mg GSH/mg anti-tumor agent |
|---|---|
| Cis-dichlorodiamineplatinum | 20–100 mg |
| Cyclophosphamide | 0.5–4 mg |
| Doxorubicin | 20–50 mg |
| Methotrexate | 0.3–15 mg |

The GSH is administered to the patient within two hours of the administration of the anti-tumor drug, and it is greatly preferred to have the glutathione administered either before, simultaneously with, or no more than 15 minutes after the administration of the anti-tumor drug. When the glutathione is administered to the patient prior to the anti-tumor drug administration, it is preferred that the glutathione be administered no more than one hour, and preferably no more than one-half hour, before the administration of the anti-tumor drug.

The present invention may be utilized to treat the tumors which are conventionally treated with the anti-tumor drugs described herein. The tumors may be both solid tumors or leukemic tumors, such as, for instance, ovarian tumors, tumors of the head and neck, and leukemia.

In the accompanying drawings, FIG. 1 represents a kit containing two vials, suitable for administration by i.v. injection using a hypodermic needle, and FIG. 2 represents another kit, containing two infusion bags, with one of the bags containing diluted GSH, and the other bag containing a suitable physiologically acceptable solution of the anti-tumor agent(s).

In FIG. 1, kit 1 includes a box 2, with vials 3 and 4 located within box 2, and protected by foam cushioning 5. Vial 3 contains a diluted GSH, and vial 4 contains a solution of one or more anti-tumor agents. If desired, of course, the box 2 can contain more than two vials, with different anti-tumor agents in a plurality of vials. This may be useful, for instance, when a solution containing two or more of the anti-tumor agents is unstable.

In FIG. 2, kit 10 includes box 11 and infusion bags 12 and 3 located within box 11. Bag 12 contains diluted GSH and bag 13 contains a solution of one or more anti-tumor agents. Again, box 10 can contain more than two infusion bags, with different anti-tumor agents in a plurality of infusion bags.

The results obtained with the anti-tumor agents tested to date suggest that reduced glutathione may be effective with all known anti-tumor chemotherapeutic agents, so far as increasing the long-term survival times of patients treated with such anti-tumor agents. Of course, it is expected that the increase in long-term survival time described herein would be obtained using reduced glutathione in combination with one or more anti-tumor agents which are developed or are the subject of publication after the filing date of the present application, and especially those anti-tumor agents which are analogs to the anti-tumor agents specifically described herein.

The compositions according to the invention may be prepared using usual methods and excipients, such as described in "Remington's Pharmaceutical Sciences Handbook", Hack Pub. Co., N.Y., U.S.A., the disclosure of which is hereby incorporated by reference.

The administration routes are those commonly used in anti-neoplastic therapy, namely the intravenous route (either by bolus or infusion) and, in case of methotrexate, also the oral route.

The most common route is however the infusional one, according to dosage regimens already established in the medical practice and which are within the skill of any expert in the art.

The infusion solution is a physiologically acceptable solution, especially a isotonic solution, which can also contain a necessary amount of salt, e.g., sodium chloride and the like, or glucose and optionally viscosity regulating compounds, such as polyethyleneglycols, polypropyleneglycols and the like.

As far as GSH is concerned, the preferred dilution is 1 g of GSH in 40 ml of a saline physiological or glucose-physiological solution, to be administered from 15 minutes to 2 hours before the administration of the antitumoral drug.

The oral administration may also be suitable for GSH and for methotrexate. In this case, suitable formulations comprise capsules, tablets, granulates, syrups, etc.

The glutathione and the anti-tumor agent may be admixed in a unit dose form. Separate unit doses are however preferred, because of the resulting flexibility of therapeutical schemes.

In the not limit the invention, the efficacy of this treatment and importance of side-effects (nausea, vomiting, myelodepression, leucopenia, piastrinopenia, nephrotoxicity, azotemia, creatinemia, urinary levels of NAG and AAP enzymes) are evaluated.

EXAMPLE 1A

A composition of cis-platinum+cyclophosphamide+GSH was administered to 7 patients suffering from advanced ovarian tumors, and that were not previously treated. The schedule of treatment was the following: cis-platinum 90 mg/m$^2$, i.v. in 250 ml normal saline over 30 min., cyclophosphamide- 600 mg/m$^2$, i.v. two hours after cis-platin, GSH 1.5 g/m$^2$ in 100 ml of normal repeated every three weeks, for 5 cycles (except for one cis-platin- This schedule was patient who received only three cycles). One patient was dropped out from the evaluation because affected by a different neoplasia (colon carcinoma). The remaining six patients (1 stage II, 4 stage III and 1 stage IV) received a standard i.v. pre and post- hydration, which consisted of 2000 ml fluids. Diuretics were not used on a routine basis. The patients received a total of 28 courses (or cycles) with GSH at 1500 g/m$^2$ dose level.

No symptoms of urotoxicity, nephrotoxicity, myelotoxicity and neurotoxicity were observed; side effects such as nausea and vomiting were very mild in contrast to those observed without GSH supplementation treatment. There was no evidence of severe myelosuppression.

First of all, the results put in evidence the lack of negative interference of GSH on the therapeutic efficacy of cis-platin. In fact 6/6 patients with advanced disease achieved complete remission (pathologically documented); five are still in remission after more than 24 months of follow-up and, unfortunately, one had relapse after 20 months of disease-free interval. She is still alive with brain metastasis after 24 months.

In spite of a small number of patients treated, it is to be pointed out that in similar occasions frequency of full remissions at two years after end of the treatment is only of the order of 5-10%.

EXAMPLE 2A

Nine patients with ovarian cancer at high risk of radical surgery received treatment with a relapse after composition of cis-platinum+cyclophosphamide+GSH. All the patients were not previously treated with other anti-neoplastic agents.

The schedule treatment was the following: cis-platinum (90 mg/m$^2$, administered i.v. in 280 ml of normal saline over 30 min.), cyclophosphamide (600 mg/m$^2$ i.v.) and GSH (3 g/m$^2$). This schedule was repeated every three weeks.

All the patients (6 stage I, 2 stage II, 1 stage III) received a reduced i.v. hydration (1000 ml fluids) and GSH (3 g/m$^2$), in 200 ml of normal saline, given i.v. over 15 min. prior to each cis-platin administration.

Diuretics were not used on a routine basis.

No nephrotoxic and neurotoxic manifestation were observed, there is no evidence of severe myelosuppression.

The side-effects were very mild as compared to the previous protocol of administration, whereas the reduced hydration, increased the patient's compliance avoiding any possible side effects due to the amount of fluids otherwise administered.

The patients were submitted to 44 courses (or cycles) up to now; five patients have no evidence of disease after the end of five courses and four are still under treatment.

The results strongly support that GSH does not reduce the anti-tumor activity of cis-platin, the use of GSH represents an alternative safer method for delivering high doses of platinum-complexes and for surprisingly increasing remission rate.

EXAMPLE 3A

A patient having an advanced and relapsing ovarian tumor previously treated with cis-platinum, was treated with a combination of cis-platinum+GSH every four weeks. Cis-platinum was administered at a weekly dosage of 200 mg/m$^2$ (40 mg/m$^2$ i.v. in normal saline at 1-5 days) for five weeks; GSH was administered i.v. at a dosage of 35 mg/ mg of cis-platinum in normal saline, 30 minutes before administration of cis-platinum. The week of administration (5 administrations) was followed by three weeks of rest, and then the cycle was repeated, and so on, for a total of 5 cycles of administration extending over 17 weeks (5 weeks of actual treatment and 12 weeks (3 weeks X 4) of rest intervals). This patient showed an extraordinary clinical response, after a first cycle of treatment, with the disappearance of an important peritoneal carcinomatous ascitis.

Generally the dosage of 200 mg/m$^2$ of cis-platinum is considered the maximum dosage limit, which is always followed by serious side-effects, after two or three weeks. The above patient did not show any side-effects due to the treatment even at the end of the 5 course or cycle period and she is still alive 6 months after the treatment.

EXAMPLE 4A

Six patients with advance head and neck cancer, pre-treated with radiotherapy and surgery, and in a relapse phase of the disease, were treated with a combination of cis-platinum: 100 mg/m$^2$ (20 mg/m$^2$ i.v. in 100 ml normal saline at days 1-5)+5-fluorouracyl: g/m$^2$ (200 mg/m$^2$ i.v. in 500 ml normal saline at days 1-5)+GSH: 5 g/m$^2$ (1 g/m$^2$ in 100 ml normal saline at days 1-5) GSH was administered 30 before cis-platinum whereas 5-fluorouracyl was administered 90' after cis-platinum. This treatment was repeated every 2 weeks for 2-4 treatments.

All patients achieved an important objective response occurring a few days after treatment. In all patients it was noticed a reduction and/or disappearance of tumoral lesions with surprising important relief in the overall conditions, one year after treatment. No side-effect was noticed.

EXAMPLE 5A

Different animal tests were carried out in order to show the effect of GSH administration in combination with an anthracycline (doxorubicin) and with methotrexate.

(1) Protective effect of glutathione (GSH) on anthracycline (doxorubicin) induced myocardiotoxicity.

Twenty-four Sprague Dawley rats, weighing 150–200 g, fed with standard diet and water "ad libitum", were randomized in 4 groups (A,B,C,D) 6 animals each.

Group A (GSH+doxorubicin):

Six animals were treated i.v. in the morning (10 am.) with glutathione g/kg) dissolved in normal saline (total injected volume 1 ml/kg). After 30 minutes, the same animals were treated i.v. with doxorubicin (3 mg/kg) dissolved in normal saline (total injected volume 1 ml/kg).

The treatment has been then repeated after 7 days, for 4 consecutive times as a whole.

Group B (Doxorubicin)

Six animals were treated similarly to group A, except that glutathione was omitted and substituted with normal saline only.

Group C (GSH):

Six animals were treated similarly to group A, except that doxorubicin was substituted with normal saline only.

Group D (control)

Six animals were treated similarly to group A except that both drugs were substituted with normal saline.

The day of the first administration was defined "zero day" and all the animals were killed after 8 weeks from the start of the experiment.

During the experiment, starting from the zero time, all the animals were evaluated weekly for body weight increase, electrocardiographic intervals Q-T and S-T.

After the 8-week experiment, the necroscopic examination allowed to evaluate for each animal the degree of myocardial lesions expressed as an average of vacuolate cells for 10 observation fields at the optical microscope (200 x).

While the treatment with only GSH did not induce, in comparison with the control group, significant changes in the different parameters under exam, in all the animals of group A the preventive treatment with GSH proved to be able to correct (body growth curve, ECG recording, decrease of the vacuolate cells number) the 1 toxic and cardiological effects found in the doxorubicin treated group B.

Equivalent results were obtained in a subsequent experiment wherein the glutathione was administered i.v. at the dose of 0.5 g/kg 30 min. before the doxorubicin administration (3 mg/kg).

(2) Cytotoxic activity of GSH+Doxorubicin on P388 in leukemia in mice.

(After i.p. administration of the drugs)

In the Table 1, the results obtained in CD2F1 mice i.p. treated at the day 0 with 106 P388 leukemia cells and treated. i.p. at the day 1 with doxorubicin (DX) (7.5 mg/kg) and/or with GSH (333 mg/mg doxorubicin) are reported.

The GSH was administered 30 min. before DX.

The experiment of the combination GSH+DX was repeated in 2 groups of animals.

TABLE 1

| Experimental groups | GSH | DX | TMS | T/C % | TOX | LTS |
|---|---|---|---|---|---|---|
| Controls | — | — | 11,4 | 100 | 0/10 | 0/10 |
| GSH | + | — | 11,3 | 99 | 0/10 | 0/10 |
| DX | — | + | 16 | 140 | 0/10 | 0/10 |
| GSH + DX | + | + | 21 | 184 | 0/10 | 2/10 |
| GSH + DX | + | + | 27 | 236 | 0/10 | 4/10 |

TMS means mean survival time in days, T/C % is a percent value of the response of drug treated animals in comparison with the control, taken as 100.

TOX means the number of treated animals died before the control animals. LTS is the number of animals survived at long term (2 months at least).

It should be stressed that the test used an experimental model, the P388 leukemia, characterized by an exclusively intraperitoneal tumor growth, i.e. a growth in the cavity wherein the insulation of the tumoral cells has been carried out.

The results, reported in Table 1, confirm that glutathione alone is devoid of any direct anti-tumoral activity, neither it is able to increase the natural defences of the inoculated animals from the tumor's aggression.

On the contrary, a preventive treatment with GSH in comparison with a subsequent treatment with anthracyclines (for instance doxorubicin) causes an unexpected increase of the anti-tumoral activity of the drug, expressed as a significant increase of the TMS, T/C % and LTS values.

(3) Effect of GSH (administered i.v.) at different doxorubicin dosages (i.p.) on P388 leukemia in mice.

The experimental conditions are similar to that of the previous test.

In these tests, the glutathione has been administered i.v., 30' before of the optional i.p. administration of anthracycline, doxorubicin.

The GSH treated animals received an equal amount of drug (1500 mg/kg) whereas the doxorubicin treated animals received i.p. scalar amounts of anthracycline. The animals consecutively treated with GSH and DX received the two drugs in the ratios of 100, 125, 150 and 200 mg of GSH per mg of DX.

The experimental results reported in Table 2 confirm that GSH, when administered i.v., is not able to exert any direct or indirect effect on the tumoral growth, neither it possesses toxic effects.

The treatment with DX shows the good efficacy, in this experimental model, of the dosage of 10 mg/kg with a T/C % of 170, the dose of 7.5 mg/kg being also slightly active, whereas the immediately higher dosage induces toxic effects.

TABLE 2

| Experimental groups | GSH (1500 mg/kg) (i.v.) | DX (mg/kg) (i.p.) | TMS | T/C % | TOX | LTS >60 days |
|---|---|---|---|---|---|---|
| Controls | — | — | 10 | 100 | 0/8 | 0/8 |
| GSH | + | — | 10,5 | 105 | 0/8 | 0/8 |
| DX | — | 15 | 6 | 60 | 8/8 | 0/8 |

TABLE 2-continued

| Experimental groups | GSH (1500 mg/kg) (i.v.) | DX (mg/kg) (i.p.) | TMS | T/C % | TOX | LTS >60 days |
|---|---|---|---|---|---|---|
| DX | — | 12,5 | 12 | 120 | 4/8 | 0/8 |
| DX | — | 10 | 17 | 170 | 0/8 | 0/8 |
| DX | — | 7,5 | 15,5 | 155 | 0/8 | 0/8 |
| GSH + DX (100)* | + | 15 | 6 | 60 | 7/8 | 0/8 |
| GSH + DX (120)* | + | 12,5 | 18 | 180 | 0/8 | 0/8 |
| GSH + DX (150)* | + | 10 | 19,5 | 195 | 0/8 | 1/8 |
| GSH + DX (200)* | + | 7,5 | 14,5 | 145 | 0/8 | 1/8 |

*mg of GSH/mg of DX

The combined treatment GSH/DX shows, for all the used weight ratios, a protective effect of the combination from the toxicity of the anti-tumor drug.

In fact, for the highest DX dose, a relatively small weight GSH/DX ratio (100 mg/mg) shows a decrease in the TOX parameter after pre-treatment with GSH from 8/8 to 7/8.

On the other side, for the lowest DX dose, a relatively high weight GSH/DX ratio such as 200 mg/mg seems to show a decrease in the anti-tumoral drug efficacy.

The T/C % decreases from 155 for the DX treatment alone (7.5 mg/kg) to a value of 149, even though a certain protective effect may be deduced from the survival of ⅛ animals after the 60th day.

A narrower dose ratio between the two drugs surprisingly evidentiates an enhancement of the anti-tumoral activity which is particularly evident at a dosage of 12.5 mg/kg of DX whereas the T/C % increases from 120 to 180 in combination with a GSH/DX ratio of 125 mg/kg and even more at the limit optimal dosage of 10 mg/kg of DX whereby the T/C % changes from 170 to a value of 195.

(4) Enhancement of the anti-tumoral effect of anthracyclines by GSH on P388 and P388 /DX resistant leukemia.

The experiments were carried out in a similar way to the experimental scheme of the previous tests 2 and 3. The glutathione was administered i.v. 30, before of doxorubicin. In the tests, whose experimental data are reported in the Tables 3 and 4, the doxorubicin is administered i.p. at a sub-optimal dose level (for the used treatment schedule), in order to evidentiate the synergic effect of the glutathione treatment.

In the test of Table 3 wherein P388 leukemic cells were inoculated, variable dosages of glutathione were used, with respect to the fixed dose of DX (7.5 mg/kg) so as to provide GSH/DX ratios respectively of 20 and 50 mg of GSH per mg of DX.

TABLE 3

GSH and Doxorubicin effect on P388 leukemia in CD2F1 mice.

| Experimental group | GSH i.v. mg/kg | DX i.p. mg/kg | GSH DX | TMS | T/C % | TOX | LTS |
|---|---|---|---|---|---|---|---|
| Controls | — | — | — | 10,2 | 100 | 0/10 | 0/10 |
| GSH | 375 | — | — | 10,4 | 101 | 0/10 | 0/10 |
| DX | — | 7,5 | — | 16,7 | 163 | 0/10 | 0/10 |
| GSH + DX | 150 | 7,5 | 20 | 20,6 | 201 | 1/10 | 0/10 |
| GSH + DX | 375 | 7,5 | 50 | 23 | 225 | 0/10 | 0/10 |

In the case of inoculation of P388/DX resistant leukemic cells an intermediate dose of glutathione was administered, corresponding to GSH/DX ratio of 25 mg/mg (total dose of GSH 187.5).

TABLE 4

Effect of GSH and doxorubicin on Pee/DX adria-resistant (resistant to DX) leukemia on CD2F1 mice.

| Experimental group | GSH i.v. mg/kg | DX i.p. mg/kg | TMS | T/C % | TOX | LTS |
|---|---|---|---|---|---|---|
| Controls | — | — | 9,6 | 100 | 0/10 | 0/10 |
| GSH | 187,5 | — | 10 | 104 | 0/10 | 0/10 |
| DX | — | 7,5 | 11,4 | 118 | 0/10 | 0/10 |
| GSH + DX | 187,5 | 7,5 | 13,8 | 143 | 0/10 | 0/10 |

The results show a clear synergism both on the sensitive and on the resistant strain.

(5) In vitro activity of GSH and methotrexate (MTX) on human HT-29 cells (colon carcinoma). Human HT-29 cells (colon carcinoma) were used; the cells were pre-treated with GSH at the concentrations of 20 and 40 mg/ml and then exposed to MTX at the concentrations of 0.05, 0.1, 0.5 and 1 mg/ml for 24 h. The concentrations causing 50% of cell death turned out to be 0.12 mg/ml in the absence of GSH and about 0.04–0.06 mg/ml in the presence of GSH. The cells were cultivated in RPMI 1640 medium+10% of fetal calf serum.

COMPOSITIONS AND METHODS FOR PROTECTING AGAINST SIDE-EFFECTS CAUSED BY ADMINISTRATION OF PLATINUM COMPOUNDS

In another embodiment, the invention concerns a pharmaceutical composition, particularly for out-patient or hospital use, characterized by an high dosage of reduced glutathione. More precisely, the invention concerns a pharmaceutical composition, particularly for out-patient or hospital use, containing, per unit dose, at least 2.5 g of reduced glutathione, and preferably 5 g of reduced glutathione, for use as protecting agent against the side-effects (particularly the nephrotoxicity) induced by platinum coordination compounds, particularly "cis-platinum".

The use of cis-diamine-dichloroplatinum (CDDP), or "cis-platinum" in antiblastic chemiotherapy is known. The remarkable nephrotoxicity induced by cis-platinum at the level of the renal tubuli is also known. The CDDP administration is therefore carried out contemporaneously with a marked hydratation of the patient by the intravenous route, both before and after the drug infusion and it is often coupled with the induction of forced diuresis by means of the combination with diuretics. Nevertheless, neither a strong hydratation nor a similarly strong forced diuresis succeed in avoiding tubular damages of remarkable seriousness following the cis-platinum treatment.

A certain degree of nephroprotective action of reduced glutathione (GSH), detected according to some parameters (azotemia, creatininemia, changes in body weight, weight ratio of the kidney to the body weight) has been previously shown in the cis-platinum treated animals (F. Zunino, O. Tofanetti et al., *Tumori* 69, 105–111, 1983. It was however noticed that even the administration of relatively enormous doses (1 g/kg body weight) of GSH did not allow to completely eliminate tubular damages both in the rat and in the mouse.

On the contrary, it has now been surprisingly found that GSH, administered to men in high doses (higher than a determined threshold value, and remarkably higher than those used for other indications) but that are much lower than those deducible from the experiences (although unsatisfactory) carried out on the animals, is able to protect not only to an almost complete extent from the cis-platinum induced tubular damages but to keep contemporaneously unchanged the therapeutic effects of cis-platinum itself.

The surprising remark above reported has been moreover made according to parameters which are much more sensitive and precise than those used in the animal tests, and particularly determining in the patients' urine the level of two microenzymes, alanine-aminopeptidase (AAP) and N-acetyl-$\beta$-glucosaminidase (NAG), which dramatically increase (about 8–10 times the normal values) in the case of tubular damages.

The importance and the significance of the AAP and NAG levels as nephrotoxicity index have been shown by different authors: see, for instance, B. R. Jones et al., "Comparison of methods of evaluating nephrotoxicity of cis-platinum", Clin. Pharmacol. Ther. 1980, 557; R. L. Sherman et al., "N-Acetyl-$\beta$-Glucosaminidase and $\beta_2$-Microglobulin. Their Urinary Excretion in Patients with Renal Parenchimal Disease", Arch. Intern. Med. 143, 1183 (1983); B. R. Mayer et al., "Increased Urinary Enzyme Excretion in Workers Exposed to Nephrotoxic Chemicals", Amer. Journ. Med. 76, 989 (1984).

Therefore, the protection from tubular damages, induced by cis-platinum, by GSH administration has been documented by the systematic dosage of AAP and NAG in the patient's urine, as hereinafter reported.

Female patients, affected by ovarian neoplasias, have been taken into account, during different cycles of cis-diamine-dichloro-platinum (CDDP) treatment at rather high doses (90 mg/m$^2$, by intravenous route). The AAP and NAG dosage in the patients' urine has been carried out in the absence and in the presence of the GSH treatment, carried out before and/or after the CDDP infusion (the GSH was always administered by slow infusion).

The dosage of the microenzyme alanine-aminopeptidase (AAP) has been carried out measuring by colorimetric assay the p-nitro-alanine released by said enzyme from the catalytic hydrolysis of alanine-p-nitroanilide (see J. E. Peters et al., Clin. Chim. Acta 37, 213 (1972); K. Jung et al., Clin. Chem. 26, 1251 (1980)). Also N-acetyl-$\beta$-glucosaminidase (NAG) has been determined by colorimetric assay, by measuring, in alkaline medium, the p-nitrophenol released by the microenzyme from p-nitrophenyl-N-acetyl-$\beta$-D-glucosaminide (see D. Marhun, Clin. Chim. Acta 73, 453 (1976); T. D. Lockwood et al., Tox. Appl. Pharmacol. 49, 323 (1979); A. M. Gressner et al., Clin. Chim. Acta 124, 315 (1982)).

50 CDDP therapeutic cycles have been altogether examined, with the results hereinafter summarized:

A. Only hydratation, without GSH treatment. AAP undergoes a mean increase of about 8 times the normal value; NAG undergoes a mean increase of about 10 times the normal value.

B. Hydratation+1 gram (in total) of GSH administered 15 minutes before or after the cis-platinum infusion; no protective action is noticed; the level of urinary enzymes AAP and NAG is substantially comparable to that determined for the group A.

C. Hydratation+2 grams (in total) of GSH administered at the rate of 1 gram 15 minutes before and 1 gram 15 minutes after the cis-platinum infusion: a sufficiently evident protective action is noticed since the dosage of the two enzymes reveals a mean increase of 5 times for AAP and of 7 times for NAG, with respect to the normal values.

D. Hydratation+2.5 grams (in total) of GSH, administered also in this case half 15 minutes before and half 15 minutes after the cis-platinum infusion: the protection is higher than in the case of C, the AAP and NAG mean levels being three times and three-four times the normal values, respectively.

E. Hydratation+5 grams (in total) of GSH, administered with the above mentioned criteria: the mean level of the two enzymes is about twice the normal value, with an almost complete patients protection.

It should be pointed out that, as already mentioned, even in group E (and consequently even in the previous groups) the therapeutic results of the cis-platinum administration remain unchanged.

The above results allow to draw the following conclusions:
(a) administration of 1 g of GSH is substantially devoid of efficacy;
(b) changing the dosage from 2 to 2.5 grams of GSH, a critical dosage is found since by increasing GSH of 5%, a 40% decrease in AAP level and even about a 50% decrease in NAG level, is obtained;
(c) the effective dose of GSH in the protection from the cis-platinum induced nephrotoxicity is remarkably higher than the GSH dosages used for other therapeutic indications; at the same time, it is at least one order of magnitude lower in comparison with that exerting in the animal a protection which is moreover yet unsatisfactory.

An essential aspect of the invention is therefore provided by pharmaceutical compositions, particularly for out-patient or hospital use, suited for the protection from platinum compound induced side-effects (particularly nephrotoxicity), containing amounts of reduced glutathione not lower than 2.5 grams per unit dose, preferably 5 grams per unit dose, optionally in admixture with excipients commonly used in pharmaceutical technique and/or with other active principles.

Non limitative examples of said pharmaceutical compositions are hereinafter reported:

EXAMPLE 1

(a) Lyophilized bottles each containing:
reduced glutathione: 2.50 g
ethylendiamine: 0.20 ml
polyvinylpyrrolidone 40,000: 0.125 g
(b) Solvent vials each containing:
water for injectable preparations: 15 ml.

EXAMPLE 2

(a) Lyophilized bottles each containing:
reduced glutathione; 5.00 g ethylendiamine: 0.40 ml
polyvinylpyrrolidone 40,000: 0.25 g
(b) Solvent vials each containing:
water for injectable preparations: 30 ml.

We claim:

1. A method of potentiating the anti-tumor activity of a platinum complex anti-tumor agent in a patient to which said anti-tumor agent is administered, said method comprising administering to said patient a potentiating amount of glutathione, wherein the amount of said glutathione is about 1500 to 3000 mg/m$^2$, and the glutathione is administered no more than 30 minutes prior to said platinum complex anti-tumor agent.

2. Method of claim 1, wherein said anti-tumor agent is cis-dichloro-diamine-platinum (II).

3. The method of claim 2, wherein the total amount of said cis-dichloro-diamine-platinum (II) administered to the patient is about 400 to 1,000 mg/m$^2$.

4. Method of claim 1, wherein a plurality of courses of treatment are used in the treatment, and in each subsequent course of treatment the amount of the cis-dichloro-diamine-platinum (II) is increased.

5. The method of claim 1, wherein the glutathione is administered simultaneously together with the anti-tumor agent.

6. The method of claim 1, wherein the glutathione is administered before the administration of the anti-tumor agent.

7. The method of claim 1, wherein the platinum complex anti-tumor agent is a pt(II)-or pt(IV)-complex.

8. The method of claim 1, wherein a second anti-tumor agent selected from the group consisting of an oxazophosphorin compound, 5-fluorouracil, methotrexate, and an anthracycline compound is administered to said patient.

9. The method of claim 8, wherein said second anti-tumor agent is administered to the patient subsequent to the administration of the platinum complex anti-tumor agent.

10. The method of claim 1, wherein the tumor is a which in the absence of said glutathione is resistant to the anti-tumor agent administered to the patient.

11. A method of protecting a patient against neurotoxicity side effects caused by the administration to the patient of an anti-tumor effective amount of a platinum anti-tumor complex, said method comprising administering to said patient 2.5 to 5 grams of glutathione no more than 30 minutes prior to the administration of the platinum anti-tumor complex.

12. In a method of treating a tumor in a patient comprising administering an anti-tumor effective amount of cis-dichloro-diamine-platinum (II) to said patient, the improvement comprising increasing the response rate of the patient to the cis-platin by administering to said patient from 20–100 mg of glutathione per mg of cis-platin no more than 30 minutes before the administration of said cis-platin.

13. A potentiated combination of compounds for treating tumors in a patient wherein the anti-tumor response rate effect of the combination is greater than the anti-tumor effect of the individual components thereof, said combination comprising an anti-tumor effective amount of at least one platinum complex anti-tumor agent, and a potentiating amount, which is about 2.5 to 5.0 grams, of glutathione.

14. Combination of claim 13, wherein the anti-tumor agent is cis-dichloro-diamine-platinum (II), and the glutathione is present in the amount of no more than 5.0 grams and from 20 to 100 mg per mg of the anti-tumor agent.

15. Combination of claim 13, wherein the combination further includes at least one second anti-tumor agent selected from the group consisting of an oxazophosphorin compound, 5 fluorouracil, methotrexate, and an anthracycline compound.

16. The method of claim 15, wherein the second anti-tumor agent is an anthracycline compound.

17. The method of claim 16, wherein said anthracycline compound is doxorubicin.

18. The method of claim 17, wherein the ratio of glutathione/doxorubicin is 20 to 50 mg of glutathione per mg of doxorubicin.

* * * * *